US00PP18626P2

(12) United States Plant Patent
Andrusiv

(10) Patent No.: US PP18,626 P2
(45) Date of Patent: Mar. 18, 2008

(54) ***BERBERIS* PLANT NAMED 'GOLDEN ROCKET'**

(50) Latin Name: *Berberis thunbergii*
Varietal Denomination: Golden Rocket

(76) Inventor: Ing. Michal Andrusiv, J Metyse 1079, Litomysl (CZ), 570 01

( * ) Notice: Subject to any disclaimer, the term of this patent is extended or adjusted under 35 U.S.C. 154(b) by 0 days.

(21) Appl. No.: 11/314,450

(22) Filed: Dec. 20, 2005

(51) Int. Cl.
*A01H 5/00* (2006.01)

(52) U.S. Cl. ..... Plt./241
(58) Field of Classification Search ..... Plt./241
See application file for complete search history.

*Primary Examiner*—Annette H Para

(57) ABSTRACT

A new cultivar of *Berberis* plant named 'GOLDEN ROCKET' that is characterized by an upright columnar habit and yellow foliage. In combination these traits set 'GOLDEN ROCKET' apart from all other existing varieties of *Berberis* known to the inventor.

1 Drawing Sheet

Genus: *Berberis.*
Species: *thunbergii.*
Denomination: 'GOLDEN ROCKET'.

BACKGROUND OF THE INVENTION

The present invention relates to a new and distinct cultivar of barberry that is grown as a dwarf shrub for container or landscape. The new cultivar is known botanically as *Berberis thunbergii* and will be referred to hereinafter by the cultivar name 'GOLDEN ROCKET'.

'GOLDEN ROCKET' was selected by the inventor in Litomysl, The Czech Republic in 1994, for unique foliage color. The new cultivar 'GOLDEN ROCKET' is a hybrid plant that resulted from cross-pollination conducted by the inventor in a cultivated area of Litomysl, The Czech Republic. Cross-pollination was between an individual plant of seed parent *Berberis thunbergii* 'Aurea' (unpatented) and an individual plant of pollen parent *Berberis thunbergii* 'Helmond Pillar' (unpatented).

The new *Berberis* variety 'GOLDEN ROCKET' is a deciduous dwarf shrub characterized by bright yellow foliage. This foliage color continues throughout the summer season. The height of the plant is three times its width. The foliage color and plant habit distinguish 'GOLDEN ROCKET' from all other *Berberis* known to the inventor.

The new *Berberis* variety 'GOLDEN ROCKET' differs from the yellow foliaged female parent plant *Berberis thunbergii* 'Aurea' in that 'GOLDEN ROCKET' is columnar. The new *Berberis* variety 'GOLDEN ROCKET' differs from the purple foliaged male parent plant *Berberis thunbergii* 'Helmond Pillar' in that 'GOLDEN ROCKET' is bright yellow in color and slightly smaller in size.

The first asexual reproduction of 'GOLDEN ROCKET' was conducted by the inventor in 1995 in a cultivated area of Litomysl, The Czech Republic. The method used for asexual propagation was vegetative cuttings. Since that time the distinguishing characteristics of 'GOLDEN ROCKET' have been determined stable and have reproduced true to type in successive generations of asexual reproduction.

SUMMARY OF THE INVENTION

The following traits have been repeatedly observed and represent the characteristics of the new *Berberis* cultivar 'GOLDEN ROCKET'. These traits in combination distinguish 'GOLDEN ROCKET' from all other commercial varieties of *Berberis* known to the inventor. 'GOLDEN ROCKET' has not been tested under all possible conditions and phenotypic differences may be observed with variations in environmental, climatic and cultural conditions, without however, any variance in genotype.

1. *Berberis* 'GOLDEN ROCKET' is a deciduous shrub.
2. *Berberis* 'GOLDEN ROCKET' is suitable for use in containers or the landscape.
3. *Berberis* 'GOLDEN ROCKET' has small white flowers in the spring.
4. *Berberis* 'GOLDEN ROCKET' exhibits an upright, columnar habit.
5. *Berberis* 'GOLDEN ROCKET' exhibits yellow foliage.
6. *Berberis* 'GOLDEN ROCKET' is propagated using vegetative cuttings.
7. *Berberis* 'GOLDEN ROCKET' is hardy to USDA Zone 5.
8. After 8 years, *Berberis* 'GOLDEN ROCKET' achieves 130 cm in height and 40 cm in width.

BRIEF DESCRIPTION OF THE DRAWING

The accompanying color drawing.

BOTANICAL DESCRIPTION OF THE PLANT

Figure 1:
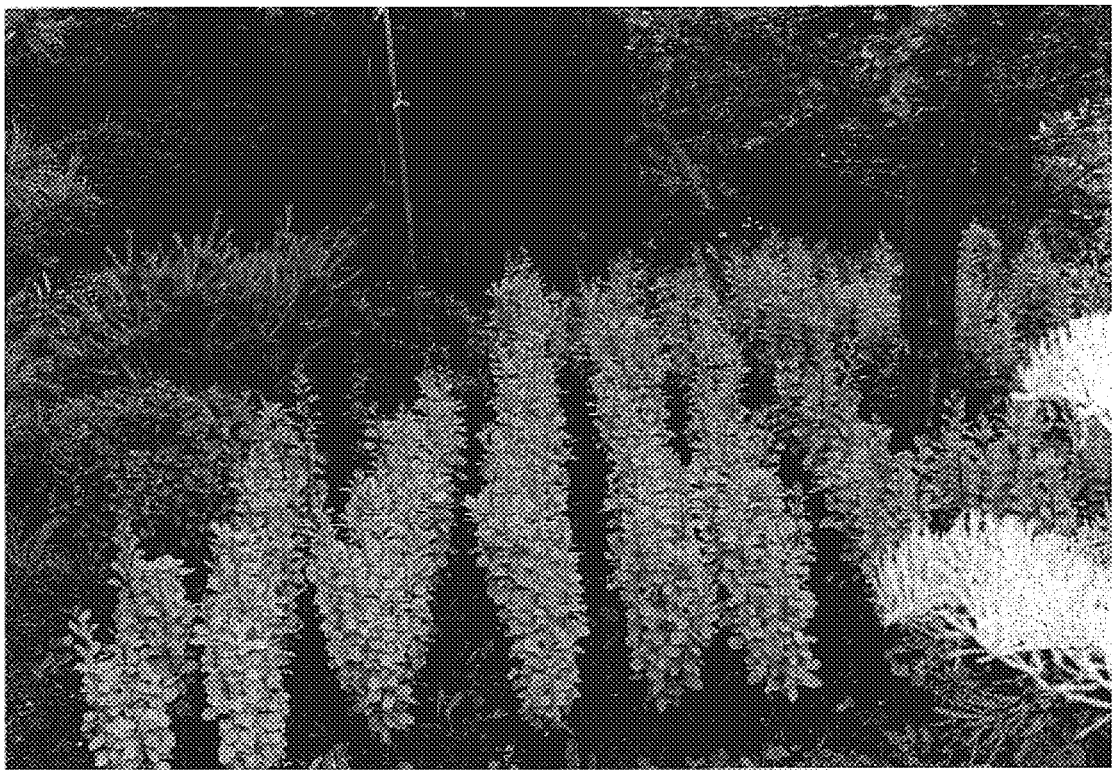
FIG. 1, illustrates the overall appearance of the new cultivar 'GOLDEN ROCKET' showing the colors as true as it is reasonably possible to obtain in colored reproductions of this type. The drawing was made in September. The plants shown in the drawing are 2-years-old grown out-of-doors in Boskoop, The Netherlands. The drawing illustrates the bright yellow foliage and upright habit of 'GOLDEN ROCKET'. Daytime temperatures averaged 15° Centigrade to 30° Centigrade. Nighttime temperatures ranged from −7° Centigrade to 14° Centigrade. The light was normal outdoor light level. No photoperiodic treatments and no growth retardants were applied to the plants. Colors in the drawing may differ from the color values cited in the detailed botanical description, which accurately describe the actual colors of the new variety of *Berberis* named 'GOLDEN ROCKET'. The drawing was made using conventional techniques and although colors may appear different from actual colors due to light reflectance they are as accurate as possible by conventional photography.

The following is a detailed description of a two year old plant of 'GOLDEN ROCKET' which has been grown in a 2-liter containers, out-of-doors in Boskoop, The Netherlands. The color determinations are in accordance with the 2001 Edition of the Colour Chart of The Royal Horticultural except where general color terms of ordinary dictionary significance are used. The growing requirements are similar to the species.

Botanical classification:
*Genus.*—*Berberis*.
*Species.*—*thunbergii.*
*Denomination.*—'GOLDEN ROCKET'.
Commercial classification: Deciduous shrub.
Use: Plant for use in containers or landscape.
Common name: Barberry.
Commercial container size: For liner production, a 5 cm round or square plug or cell or container; for planting in the garden or landscape, a 1 gallon or equivalent or larger container.
Cultural requirements: Plant in full sun to light shade in well-drained soil with moderate to regular water.
Parentage: *Berberis* 'GOLDEN ROCKET' is a hybrid plant that resulted from cross-pollination of the following parents:
*Seed parent.*—*Berberis thunbergii* 'Aurea'.
*Pollen parent.*—*Berberis thunbergii* 'Helmond Pillar'.
Plant description:
*Bloom period.*—Beginning in spring.
*Plant habit.*—Upright habit.
*Overall plant shape.*—Columnar.
*Vigor.*—Low.
*Root system.*—Fibrous roots.
*Plant dimensions.*—130 cm in height and 40 cm in width after 8 years.
*Growth rate.*—Height increases by approximately 15 cm per year.
*Hardiness.*—USDA Zone 4.
*Propagation.*—Propagation is accomplished using stem tip or internodal cuttings.
*Rooting time.*—An average of 6 weeks is needed for an initial cutting to develop roots.
*Crop time.*—24 months are needed to produce a commercial 2-liter container from a rooted cutting.
*Special growing considerations.*—Pinching back improves branching.
*Disease resistance and susceptibility.*—Not more susceptible to pests and diseases than other *Berberis thunbergii* cultivars known to the inventor. USDA-ARS, Cereal Disease Laboratory completed testing and found the cultivar resistant to Wheat Stem Rust.
Stem:
*Dimensions, main stem.*—30 cm in length and 6 mm in diameter at the base, 2 mm in diameter where the stem is in new growth.
*Dimensions, secondary stem:* 30 mm–40 mm in length; 1.5 mm in width.
*Surface.*—Smooth, slightly glossy.
*Stem color, new growth.*—N163B.
*Stem color, mature growth.*—166A.
Spines: Present.
*Dimensions.*—5 mm in length.
*Arrangement.*—Singly and alternate.
*Angle.*—90° on stem.
*Color.*—200B.
Foliage:
*Type.*—Deciduous.
*Arrangement.*—Alternate.
*Leaf dimensions.*—2 cm–3 cm in length, and 1.5 cm–2 cm in width.
*Color, mature (adaxial).*—151B, becoming 1B when fully exposed to direct sun.
*Color, mature* (*abaxial*).—147C.
*Color, immature, new tip growth,* (*both surfaces*).—N163B.
*Texture* (*both surfaces*).—Glabrous.
*Durability of leaf to stress.*—Moderate to high.
*Shape.*—Obovate to spatulate.
*Margins.*—Entire.
*Apex.*—Acute.
*Base.*—Acuminate.
*Venation pattern.*—One single central vein from the base. No visible lateral veins.
*Attachment.*—Sessile to petiolate.
*Petiole length* (*when present*).—1 mm–8 mm.
*Pubescence* (*adaxial and abaxial surfaces*).—None present.
*Leaf surface* (*adaxial and abaxial surfaces*).—Glabrous.
Fragrance: None.
Flowers:
*First appearance.*—April.
*Flowering period.*—April–June.
*Inflorescence form.*—Sparse, axillary raceme.
*Color.*—155A.
*Dimensions.*—10 mm–15 mm in diameter, 6 mm–12 mm in depth.
*Pedicel.*—12 mm.
Fruit:
*Shape.*—Ellipsoid.
*Dimensions.*—Length 15 mm, diameter 10 mm.
*Color.*—43A, but brighter.
*Firmness.*—Solid, juicy.
Seeds: None observed.

What is claimed is:

1. A new and distinct cultivar of *Berberis* plant named 'GOLDEN ROCKET', as described and illustrated here within.

* * * * *